(12) United States Patent
Herzog

(10) Patent No.: US 10,145,397 B2
(45) Date of Patent: Dec. 4, 2018

(54) TWO AXIS VARIABLE CLAMP ASSEMBLY

(71) Applicant: Kenneth J. Herzog, Hampton Bays, NY (US)

(72) Inventor: Kenneth J. Herzog, Hampton Bays, NY (US)

(*) Notice: Subject to any disclaimer, the term of this patent is extended or adjusted under 35 U.S.C. 154(b) by 0 days.

(21) Appl. No.: 15/667,224

(22) Filed: Aug. 2, 2017

(65) Prior Publication Data

US 2017/0328389 A1 Nov. 16, 2017

Related U.S. Application Data

(63) Continuation of application No. 15/347,215, filed on Nov. 9, 2016, now Pat. No. 9,752,602, which is a continuation of application No. 14/735,354, filed on Jun. 10, 2015, now Pat. No. 9,518,698, which is a continuation of application No. 13/477,685, filed on May 22, 2012, now Pat. No. 9,068,690.

(51) Int. Cl.
| | | |
|---|---|---|
| *A47F 5/00* | (2006.01) | |
| *F16B 2/06* | (2006.01) | |
| *F16M 11/04* | (2006.01) | |
| *F16M 13/02* | (2006.01) | |
| *F16B 7/04* | (2006.01) | |
| *G01N 21/84* | (2006.01) | |
| *G02B 6/44* | (2006.01) | |

(52) U.S. Cl.
CPC ............ *F16B 2/065* (2013.01); *F16B 7/0493* (2013.01); *F16M 11/043* (2013.01); *F16M 13/022* (2013.01); *G01N 21/84* (2013.01); *G02B 6/4471* (2013.01); *G01N 2021/845* (2013.01)

(58) Field of Classification Search
CPC ........ F16M 11/10; F16M 13/02; F16M 11/04; F16M 11/2014; F16M 11/12; F16M 2200/022; F16M 2200/024; F16M 11/105; F16M 11/24; F16M 2200/041; F16M 13/00; F16M 11/08; F16M 11/2021; F16M 2200/08; F16M 11/041; F16M 11/18; F16M 11/2064; F16M 13/022; F16M 2200/044; F16M 2200/068; F16M 11/06; F16M 11/38; F16M 11/14; F16M 2200/027; F16M 2200/061; F16M 11/28; F16M 13/027
USPC ...... 248/292.14, 197.21, 286.1, 287.1, 285.1
See application file for complete search history.

(56) References Cited

U.S. PATENT DOCUMENTS

| | | |
|---|---|---|
| 3,647,051 A | 3/1972 | Didas |
| 4,225,035 A | 9/1980 | Mohney et al. |
| 4,502,594 A | 3/1985 | Sijbrandij |
| 5,335,782 A | 8/1994 | Herzog |
| 6,019,326 A | 2/2000 | Baerwolf et al. |
| 6,302,280 B1 | 10/2001 | Bermes |
| 6,764,055 B1 | 7/2004 | Lee |
| 7,152,836 B2 | 12/2006 | Pfister |
| 7,293,667 B2 | 11/2007 | Flynn |
| 7,510,156 B1 | 3/2009 | Yaeger |
| 7,578,492 B2 | 8/2009 | Darre' |
| 7,717,375 B2 | 5/2010 | Chen |

(Continued)

*Primary Examiner* — Steven M Marsh
(74) *Attorney, Agent, or Firm* — Amster, Rothstein & Ebenstein LLP

(57) ABSTRACT

A clamp assembly includes a single adjustment mechanism that allows for adjustment of an object supported on the clamp assembly along two axes. The adjustment mechanism connects to a bracket and a support rod on which the object is mounted to lock a desired position of the object in place when desired and to allow for adjustment of that position, when desired.

15 Claims, 3 Drawing Sheets

(56) References Cited

U.S. PATENT DOCUMENTS

| | | |
|---|---|---|
| 8,282,052 B2 | 10/2012 | Huang |
| 2003/0213882 A1 | 11/2003 | Chen |
| 2012/0104807 A1 | 5/2012 | Lauchie et al. |

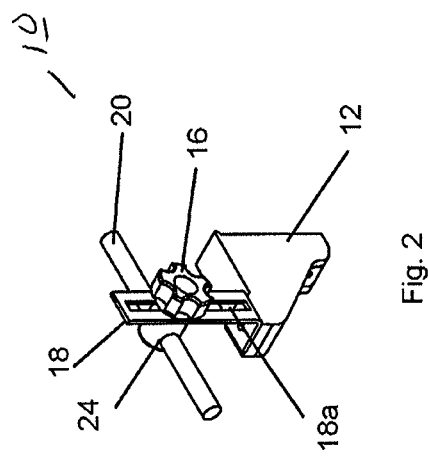
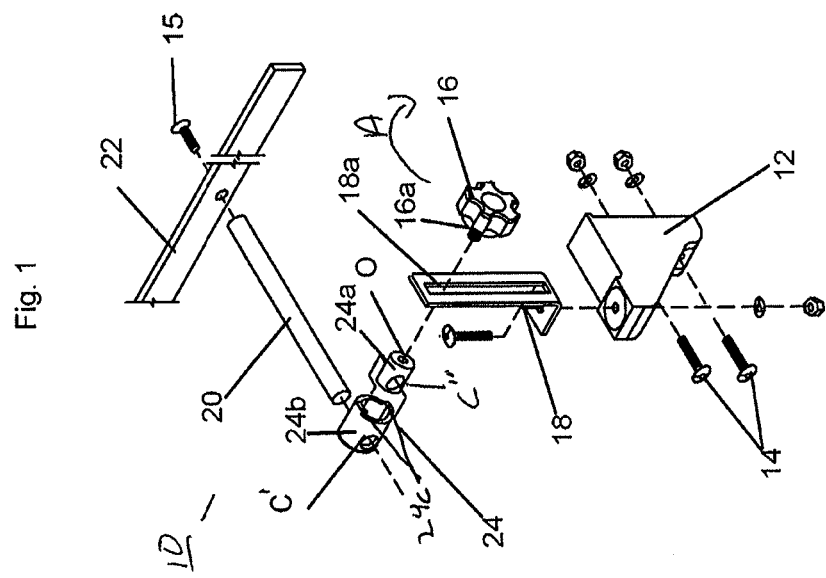

TWO AXIS VARIABLE CLAMP ASSEMBLY

The present application is a continuation under 37 C.F.R. § 1.53(b) of prior U.S. application Ser. No. 15/347,215, filed Nov. 9, 2016, which is a continuation of Ser. No. 14/735,354, filed Jun. 10, 2015, now U.S. Pat. No. 9,518,698, issued Dec. 13, 2016, which is a continuation of Ser. No. 13/477,685, filed May 22, 2012, now U.S. Pat. No. 9,068,690, issued Jun. 30, 2015, entitled "TWO AXIS VARIABLE CLAMP ASSEMBLY," the entire contents of which are hereby incorporated herein by reference.

BACKGROUND

Field of the Disclosure

The present disclosure relates to a clamp assembly that allows for adjustment of a position of an object supported thereon along two axes via actuation of a single adjustment mechanism.

Related Art

Clamp assemblies are commonly used in various assemblies to hold objects in a desired position. For example, it is common to provide a clamp assembly, or assemblies, that are fastened to the frame of a conveyor system, to hold guide rails that guide products along the conveyor belt at desired positions. Clamp assemblies typically allow for adjustment of the rail upward and downward and also laterally, or horizontally, accommodating different items on the conveyor belt. Clamp assemblies are used in many other applications as well, outside of conveyor belt systems.

Typically, at least two different adjustment devices are necessary in order to allow for adjustment along two axes. While this is acceptable, it complicates adjustment somewhat since the user must make two separate adjustments to provide the desired positioning of the guide rail.

Accordingly, it would be desirable to provide a clamp assembly that avoids these and other problems.

SUMMARY

It is an object of the present disclosure to provide a clamp assembly that allows for adjustment of a position of an object supported thereon along two axes via a single adjustment mechanism.

A clamp assembly in accordance with an embodiment of the present disclosure includes a base, a bracket extending from the base, the bracket including a slot formed longitudinally therein, an adjustment knob positioned on a first side of the bracket, the adjustment knob including a shaft extending through the slot formed in the bracket, a connector positioned on a second side of the bracket, opposite the first side, and including an opening configured to receive the shaft of the knob and to releasably secure the knob to the connector and the bracket such that a position of the knob and connector is adjustable relative to a length of the bracket; and a support rod movably mounted in the connector, such that a position of the support rod relative to the connector is adjustable by operation of the adjustment knob.

Other features and advantages of the present invention will become apparent from the following description of the invention which refers to the accompanying drawings.

BRIEF DESCRIPTION OF THE DRAWINGS

FIG. 1 is an exploded view of a clamp assembly in accordance with an embodiment of the present application.

FIG. 2 is another illustration of the clamp assembly of FIG. 1.

DETAILED DESCRIPTION OF THE EMBODIMENTS

FIG. 1 illustrates an exploded view of a clamp assembly 10 in accordance with an embodiment of the present disclosure. The clamp assembly 10 preferably includes a base 12 configured for connection to the frame (not shown) of a conveyor belt system, for example. While the present disclosure discusses use of the clamp assembly 10 in a conveyor belt system, the clamp assembly is not limited to use with a conveyor belt. Indeed, the clamp assembly 10 of the present disclosure may be used in many different environments.

Figure 5:
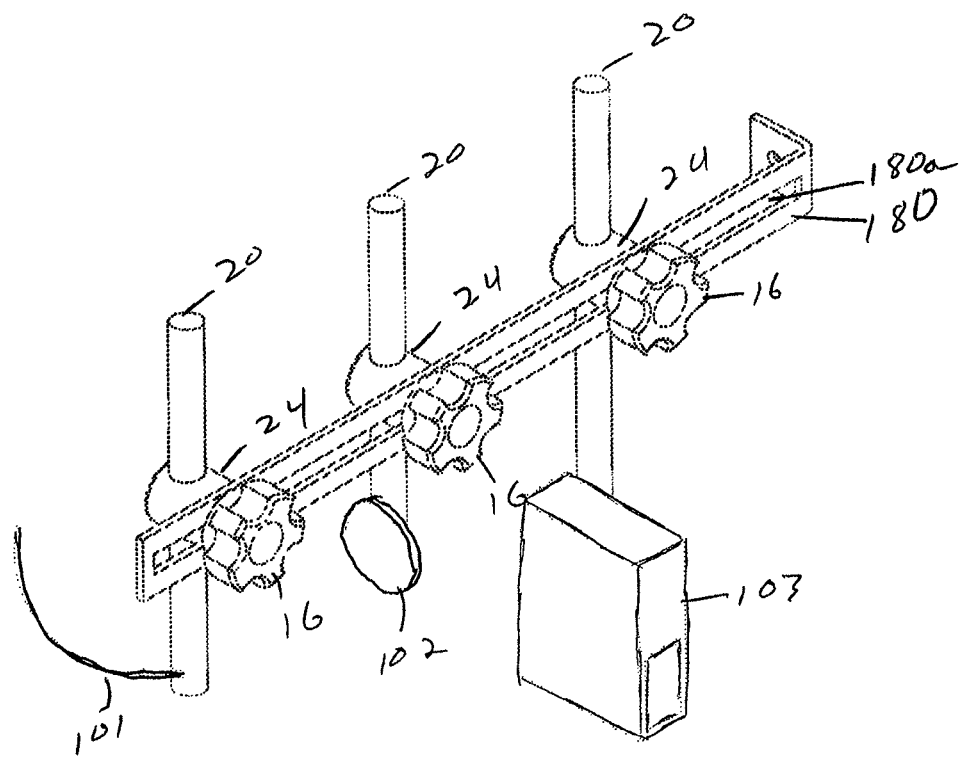
FIG. 5 illustrates a clamp assembly in accordance with another embodiment of the present application.

The base 12 may be fastened to the frame, or other element, via one or more screws 14, as illustrated in FIG. 1, however, any suitable fastener may be used. Further, while the clamp assembly 10 is discussed herein as supporting a guide rail for a conveyor belt system, as noted above, it is not limited to use in a conveyor belt system, nor is it limited to use in supporting a rail. For example, as illustrated in FIG. 5, the clamp assembly 10 may be used to support a wide variety of items, including, but not limited to sensors 103, reflectors 102 and fiber optic cables 101.

In FIG. 1, a vertical bracket 18 is mounted on top of the base 12 and extends upward therefrom. While FIG. 1 illustrates the bracket 18 extending vertically, the bracket may extend in other directions as well. For example, as can be seen in FIG. 5, the bracket 18 may extend horizontally. An elongated central slot 18a is formed in the bracket 18 and extends the length of the bracket. The slot 18a accommodates a threaded shaft 16a connected to adjustment knob 16 at one end on an outer surface of the bracket 18. An opposite end of the shaft 16a extends into a connector 24 that is provided on the inner surface of the bracket 18. The knob 16 and connector 24 are fastened to the bracket 18 to maintain a desired position of the connector 24 on the bracket. This further sets the position of the guide rail 22 fastened thereto. Specifically, the threads on the shaft 16a engage internal threads formed in opening O of the connector 24 to the secure the knob 16 and connector 24 to the bracket 18. While the shaft 16a preferably includes threads that engage corresponding threads in the connector 24, any other suitable adjustable fastener may be used to connect the knob 16 to the connector.

The knob 16 is rotated in a first direction (See Arrow A of FIG. 1) to tighten the connection between the knob 16, the connector 24 and the bracket 18 to set a position for the rail 22, or other element, connected to the connector 24 via support rod 20. Rotation of the knob 16 in the opposite direction loosens the connection between the knob 16 and the connector 24 and the bracket 18 such that the knob 16 and connector 24 may slide in the slot 18a to adjust the position thereof.

Figure 3:
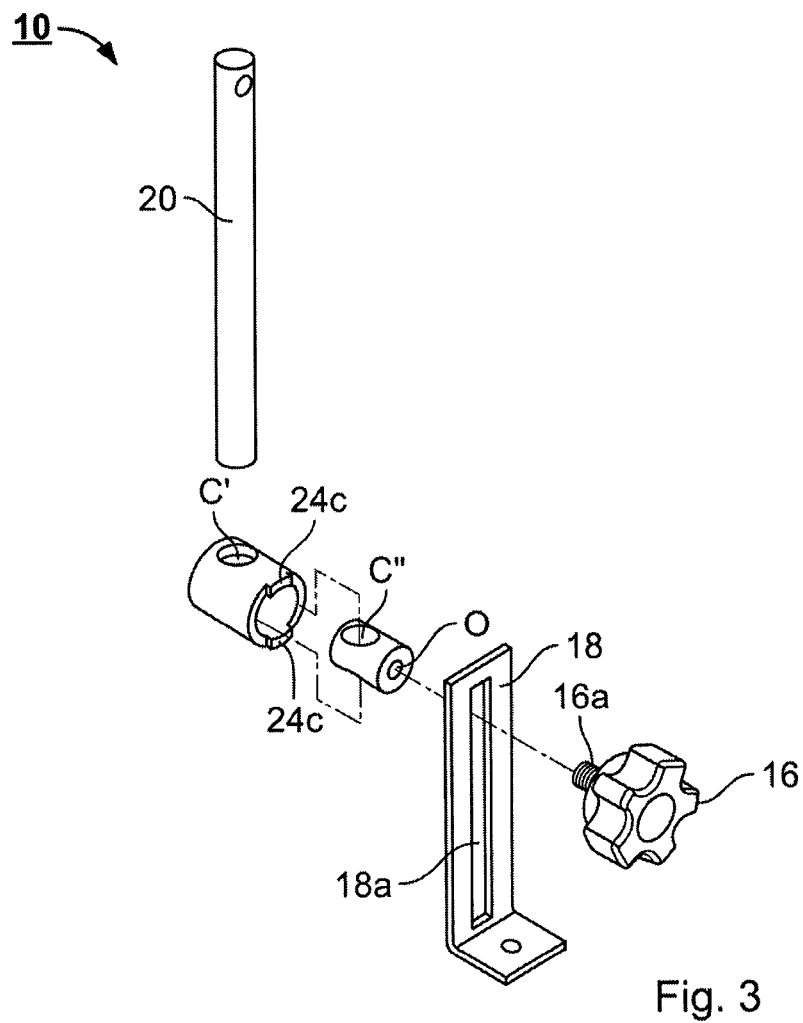
FIG. 3 is an exploded view of a clamp assembly in accordance with another embodiment of the present application.
Figure 4:
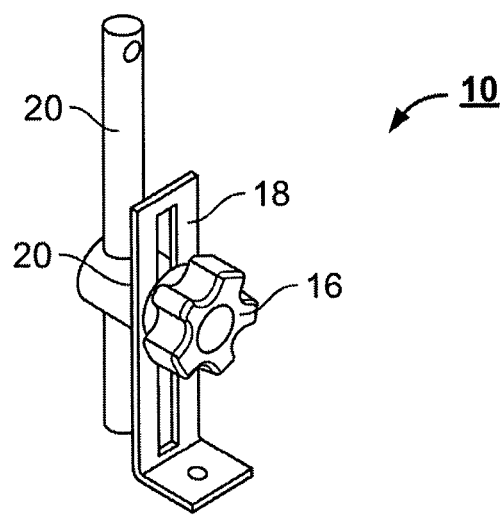
FIG. 4 is another illustration of the clamp assembly of FIG. 3.

The connector 24 includes an outer element 24b and an inner element 24a. The outer element 24b and the inner element 24a are preferably cylindrically shaped. The inner element 24a slides into the outer element 24b. A rod channel C' is provided in the side of the outer element 24b. A second rod channel C" is formed in the side of the inner element 24a. The threaded shaft 16a extends into the inner element 24a and engages threads on the inner surface of opening O. The support rod 20 extends through the channels C', C". The support rod 20 may be used to support the guide rail 22 to establish a position thereof. The support rod 20, however, may be used to support other objects as well, such as the sensor 103, reflector 102, and fiber optic cables 101 illustrated in FIG. 5, for example. The rod 20 is slidable in the channels C', C" when the channels are aligned to adjust the position of the rod relative to connector 24. In FIGS. 1-2, the rod 20 is slidable in a horizontal direction. In FIGS. 3-5, the rod 20 is slidable in a vertical direction. The orientation of the channels C', C" may be modified, however, to allow for sliding of the rod 20 in virtually any direction, as desired.

The rod 20 is locked into place when the knob 16 is rotated in a first direction (See Arrow A of FIG. 1) to draw the inner element 24a of the connector 24 toward the knob 16, and thus, move the channel C" out of alignment with the channel C'. A pair of teeth 24c extend inward from the inner edge of the outer element 24b and are positioned in the slot 18b of the bracket 18 to keep the outer element from rotating with the knob 16. A single tooth may be used in place of the pair of teeth illustrated in FIG. 1. Thus, as the knob 16 is rotated, the threaded shaft 16a engages the threads in the opening O to draw the inner element 24a toward the knob 16. When the knob 16 is rotated in the opposite direction, the threaded shaft engages with the threads in the opening O to push the inner element 24a away from the knob and move the channel C" back into alignment with the channel C'. This allows the position of the rod 20 to be adjusted. The rod 20 may be secured to the rail 22 via screw 15, or any other suitable fastener. Further, as is noted above, the rod 20 need not be secured to a rail, but may be secured to any desired object.

Further, when the knob 16 is rotated sufficiently in the opposite direction, the connection between the knob 16 and the connector 24 is loosened, such that the knob 16 and connector 24 can be repositioned relative to the bracket 18, as well. In this manner, rotation of the single knob 16 may be used to adjust positioning of the connector 24 and rod 20 along two axes. In this manner, the horizontal, or lateral position, of the rail 22, or other object connected to the rod 20 may be adjusted. Further, the rod 20 may be mounted in the connector 24 to allow for adjustment along other axes, if desired as shown in FIGS. 3-4, for example. After the desired position is set, the knob 16 is rotated in the first direction to secure the position.

The clamp assembly 10 of the present application thus allows for adjustment of the position of the guide rail 22, or other item, along two axes by manipulation of a single knob 16.

FIGS. 3-4 illustrate an embodiment of the clamp assembly 10 in which the rod 20 is slidable relative to the connector 24 in the same direction as the knob 16 and connector 24 are movable relative to the bracket 18. In this embodiment, the orientation of the teeth 24c relative to the channels C' C" is offset by 90 degrees compared to the embodiment of FIGS. 1-2. Otherwise, operation of the clamp assembly 10 in FIGS. 3-4 is substantially the same as that that described above with reference to FIGS. 1-2. The teeth 24c may be offset at other positions to allow the adjustment of the rod 20 in different directions, as desired.

In FIG. 5, a single bracket 180 is used in conjunction with several connectors 24, knobs 16 and rods 20. The operation of the connectors 24, knobs 16 and rods 20 relative to the bracket 180, however, is substantially the same as that described above with respect to the bracket 18. The bracket 180 includes slot 180a through which the shaft 16a of each knob extends to connect with a respective connector 24. FIG. 5 also shows some of the additional elements that may be mounted on the support rod 20 if desired, for example, fiber optic cables 101, a reflector 102 or a sensor 103. The sensor may be any desired type of sensor, including, but not limited to an optical sensor and a temperature sensor. The sensor 103 may be a bar code scanner, for example.

Although the present invention has been described in relation to particular embodiments thereof, many other variations and modifications and other uses will become apparent to those skilled in the art.

What is claimed is:

1. A clamp assembly comprising:
a first element including an opening formed therein;
an adjustment element positioned on a first side of the first element and including a shaft extending through the opening, the adjustment element rotatable relative to the first element;
a connector positioned on a second side of the first element and including an opening configured to receive the shaft of the adjustment element and to releasably secure the adjustment element to the connector such that the adjustment element and connector are movable relative to the first element; and
a support element movably mounted in the connector, such that a position of the support element relative to the connector is adjustable;
wherein the shaft of the adjustment element is threaded and rotation of the adjustment element in a first direction secures the adjustment element to the connector and the first element and rotation of the adjustment element in a second direction, opposite the first direction, loosens a connection between the adjustment element, connector and first element such that the adjustment element and connector are movable relative to the first element; and
wherein the connector includes:
an outer element including a first channel opening formed in a side thereof; and
an inner element including a second channel opening formed in a side thereof and an opening configured to receive the shaft of the adjustment element formed in an inner end thereof facing the first element, the inner element slidably mounted in the outer element such that the second channel is movable into and out of alignment with the first channel; the support element passing through the first channel and the second channel such that the support element is movable relative to the connector when the first channel and second channel are in alignment.

2. The clamp assembly of claim 1, wherein the opening includes a thread configured to interact with the threaded shaft of the adjustment element to selectively lock a position of the support element relative to the connector.

3. The clamp assembly of claim 2, wherein the outer element includes at least one tooth extending from an inner end thereof toward the first element and configured to fit in the opening of the first element to prevent the outer element from rotating relative to the first element.

4. The clamp assembly of claim 3, wherein the threaded shaft engages the threads of the opening to slide the inner element toward the first element when the adjustment knob is turned in the first direction to move the second rod channel out of alignment with the first rod channel and lock the position of the support rod relative to the connector.

5. The clamp assembly of claim 4, wherein the threaded shaft engages the threads of the opening to slide the inner element away from the first element when the adjustment element is turned in the second direction to move the second rod channel into alignment with the first rod channel and allow movement of the support element relative to the connector.

6. The clamp assembly of claim 1, further comprising a sensor mounted on the support element and held in a desired position with the clamp assembly.

7. The clamp assembly of claim 1, further comprising a reflector mounted on the support element and held in a desired position by the clamp assembly.

8. The clamp assembly of claim 1, further comprising at least one fiber optic cable mounted on the support element and held in a desired position by the clamp assembly.

9. The clamp assembly of claim 1, wherein the first element extends vertically.

10. The clamp assembly of claim 9, where the support element is movable horizontally relative to the connector.

11. The clamp assembly of claim 9, wherein the support element is movable vertically relative to the connector.

12. The clamp assembly of claim 1, wherein the first element extends horizontally.

13. The clamp assembly of claim 12, wherein the support element is movable horizontally relative to the connector.

14. The clamp assembly of claim 12, wherein the support element is movable vertically relative to the connector.

15. A clamp assembly comprising:
an adjustment member including a shaft;
a connector including an opening configured to receive the shaft of the adjustment member and to releasably secure the adjustment member to the connector with a gap formed between an inner surface of the adjustment member and a facing surface of the connector such that a size of the gap is adjustable; and
a supported element movably mounted in the connector, such that a position of the supported element relative to the connector is adjustable;
where rotation of the adjustment member in a first direction narrows the gap formed between the inner surface of the adjustment member and the facing surface of the connector and rotation of the adjustment member in a second direction, opposite the first direction, widens the gap formed between the inner surface of the adjustment member and the facing surface of the connector.

* * * * *